United States Patent [19]

Klardie et al.

[11] Patent Number: 5,782,918
[45] Date of Patent: Jul. 21, 1998

[54] IMPLANT ABUTMENT SYSTEM

[75] Inventors: Michael Robert Klardie, Birmingham; Ralph Eugene Anstaett, Alabaster; Aubrey Clint Folsom, Pelham, all of Ala.

[73] Assignee: Folsom Metal Products, Birmingham, Ala.

[21] Appl. No.: 762,881

[22] Filed: Dec. 12, 1996

[51] Int. Cl.$^6$ .................................................. A61F 2/28
[52] U.S. Cl. .............................. 623/16; 433/172; 433/173; 606/60
[58] Field of Search .............................. 433/173, 172, 433/174, 175, 176, 201.1; 606/60, 62, 63; 623/76

[56] References Cited

U.S. PATENT DOCUMENTS

| | | | |
|---|---|---|---|
| 5,174,755 | 12/1992 | Fukuda | 433/173 |
| 5,195,892 | 3/1993 | Gersberg | 433/174 |
| 5,344,457 | 9/1994 | Pilliar et al. | 623/16 |
| 5,564,921 | 10/1996 | Marlin | 433/172 |
| 5,567,155 | 10/1996 | Hansen | 433/172 |
| 5,607,304 | 3/1997 | Bailey et al. | 433/173 |

*Primary Examiner*—Paul B. Prebilic
*Attorney, Agent, or Firm*—Veal & Associates

[57] ABSTRACT

An implant abutment system uses a combination of an implant anchor, an abutment having a plurality of connection features for connecting to the implant, and a locking pin for locking the abutment into the implant. The implant anchor includes an axial bore on a superior end having inner surface features matching outer surface features of the inferior end of the abutment. The cooperative operation of these features prevents abutment rotation once the abutment is positioned within the implant and also provides indexability for angled abutments. Such anti-rotation features are accomplished with matching splines and flutes machined on the cooperative surfaces between the abutment exterior and the implant bore inner surface. The invention also provides a retention feature for locking the abutment into the implant consisting of a resilient segmented end having a retention surface positioned to match a cooperatively formed surface in the implant bore. Upon full insertion of the abutment into the implant bore, the segmented end snap-fits into the implant bore, thereby mating the retention surfaces. The abutment also has an axial bore which allows a locking pin to be threadedly inserted into the abutment bore. Upon full insertion into the abutment bore, the segmented end radial movement of the segments is prevented, thereby locking the abutment within the implant. The combination of cooperatively mated surface features on the abutment and implant prevents any possibility of axial, lateral, or rotational movement of the abutment relative to the implant, and resists torsional loading and the associated problems of such loading such as increased prosthetic maintenance and catastrophic implant failure.

18 Claims, 3 Drawing Sheets

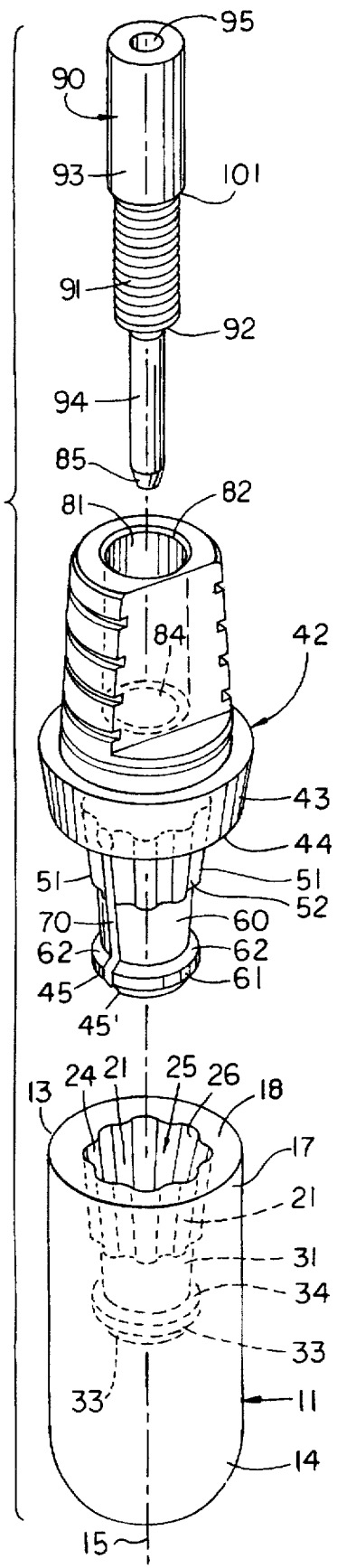
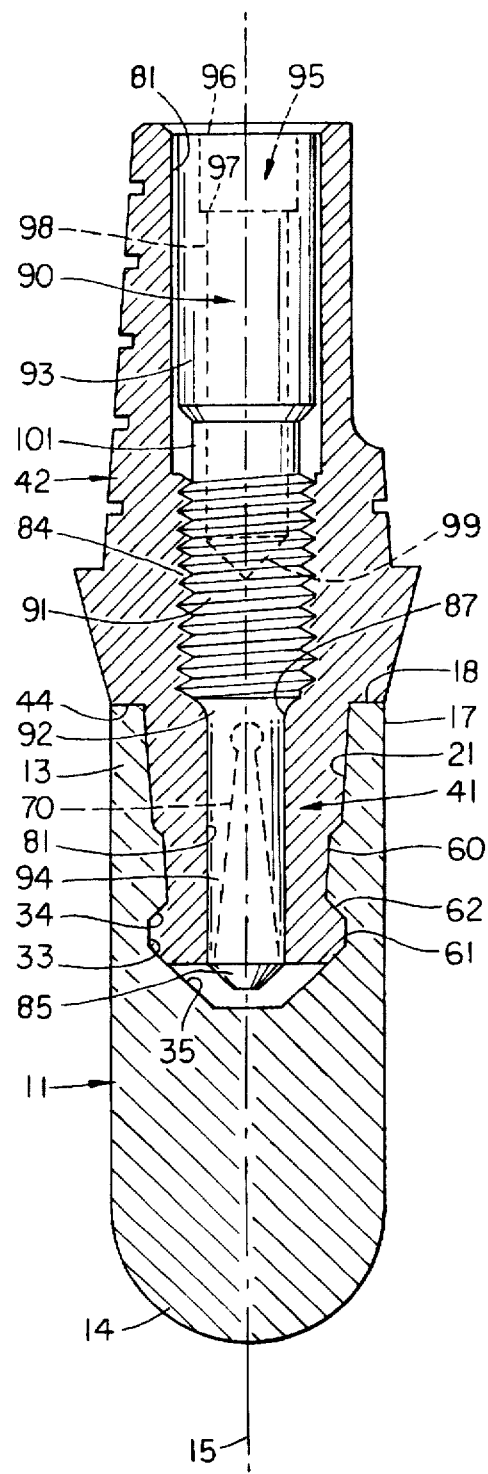

FIG. 5A
FIG. 5B
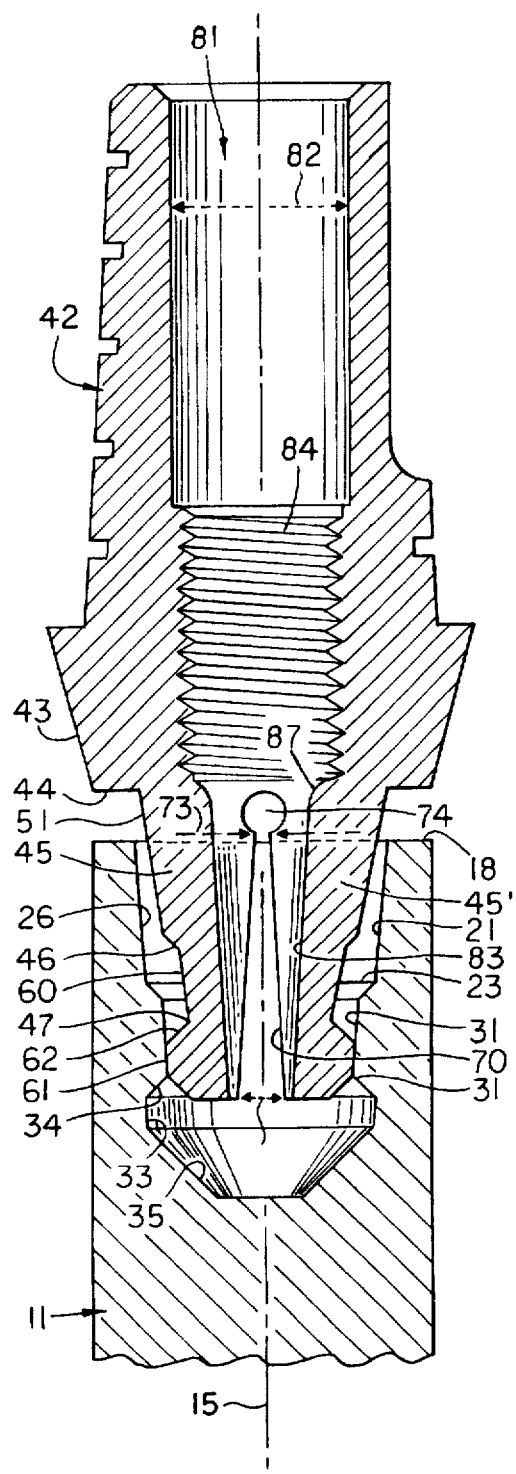
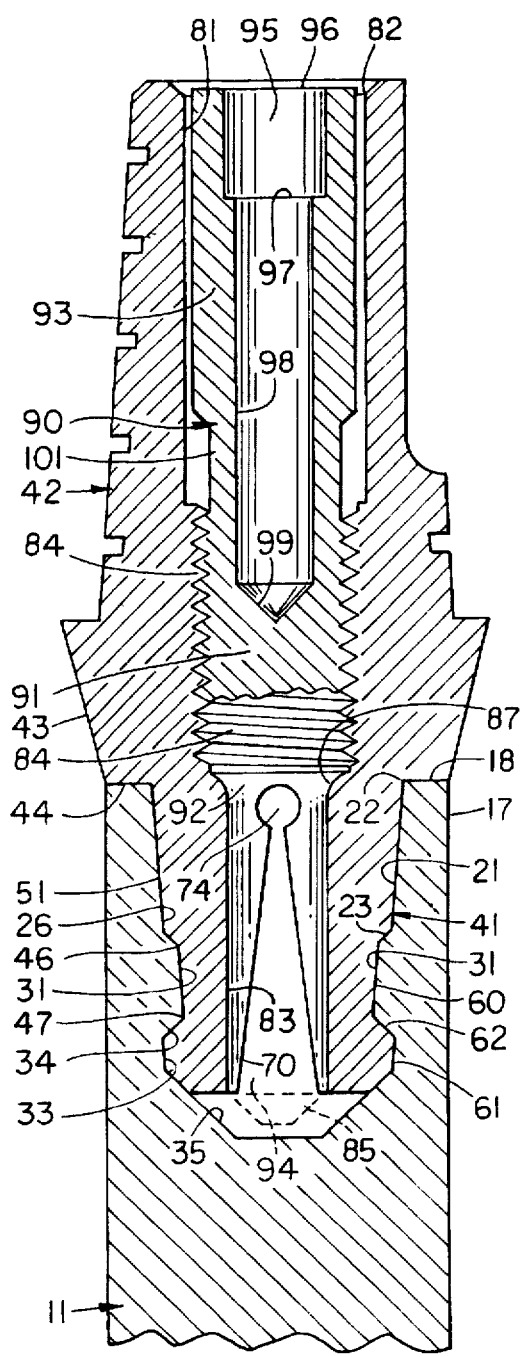

IMPLANT ABUTMENT SYSTEM

FIELD OF THE INVENTION

The present invention relates to the field of medical implant technology, and more particularly to abutment systems used to connect the implant anchor to a prosthetic device. In greater particularity, the invention relates to anti-rotation and retention features used by an abutment system to resist loosening of the abutment due to torsional loading.

BACKGROUND OF THE INVENTION

The art of implants extends back, at least, into the last century; however, only in the last twenty-five years have implants such as hip replacements, knee replacements and dental implants been widely used. These devices often employ threaded connections to fasten components of the prosthetic assembly together. However, threaded connections of the components of an implant assembly have inherent disadvantages. Reported problems noted by practitioners are breakage of the screw and loosening of the screw fixating the prosthesis in U.S. Pat. No. 5,213,500, for example. Also, the small size of the components of abutment assemblies make it difficult to install the abutment screws in the assemblies, which can lead to over-torquing of the screws facilitating failure. Furthermore, yielding may lead to a loss of preload tension in the connection, causing relative motion between the joined components and compromising the function of the prosthesis. These stress concentrations are compounded by the physical size restraints placed on prosthetic components. The materials which are available to the implant designer such as, polymers, metals, and composites, quite often exhibit creep characteristics. The stress-raising factors encountered in implants aggravate the tendency of these materials to have time-dependent strain at stress levels below yield.

Current dental implant anchors are made from biocompatible materials and are inserted into the bone of the mandible or maxilla. After an initial healing time to allow for osseointegration of the dental implant anchor, an abutment is attached to the implant anchor head. The abutment extends the implant through the soft tissue layers and provides an attachment site for the dental prosthesis, such as bridge work or a single tooth replacement.

The most common form of attachment currently in use is a small screw which passes through the abutment and threads into the implant anchor body. This abutment screw works in conjunction with a hex or spline feature on the exterior or interior of the implant anchor body. The combination of the hex feature and screw fastening secure the abutment in place and provide for anti-rotation of the abutment in relation to the implant. The hex feature is also used as a wrenching surface to install externally threaded implants into the mandible or maxilla.

An example of an external hex abutment connector is disclosed by Niznick et al. in U.S. Pat. No. 5,433,606. An example of an internal slot, hex, or spline abutment connector secured into the implant body by an abutment screw is disclosed in U.S. Pat. Nos. 4,713,003; 5,061,181; and 5,195,892.

Symington et al. in U.S. Pat. No. 4,713,003 discloses an abutment having a transverse protrusion formed on a lower surface thereof and fitting into a cooperatively formed slot in the implant anchor. A screw passes through the abutment and secures the abutment to the implant in an anti-rotational manner.

Niznick in U.S. Pat. No. 5,061,181 discloses an implant anchor which includes an axial bore having a hexagonally shaped internal surface. The inner surface of the bore also has a threaded section for receiving a prosthetic post.

Gersberg in U.S. Pat. No. 5,195,892 discloses an internally splined implant anchor adapted for receiving a cooperatively splined prosthetic support structure (abutment). A threaded fixation screw secures the abutment into the implant in a conventional manner.

Other examples of internal connectors utilizing a screw threaded through the abutment and into the implant body for securing the abutment are disclosed in Schulte et al., U.S. Pat. No. 5,199,873, Durr et al., U.S. Pat. No. 5,125,840, and Sulc, U.S. Pat. No. 5,195,891. Sulc uses a slotted lower projection on an angled support allowing for rotation of the support in relation to the abutment to a desired angular position prior to permanent attachment of the abutment to the implant. Upon marking the desired position, the support and abutment are removed from the implant and cemented together in a conventional manner, then rethreaded into the implant. These references and all the prior examples utilize a screw that either passes through or is a part of the abutment and directly engages the implant body.

Internal connectors utilizing threaded screws to hold the abutment suffer from several fundamental problems. One problem is that the small abutment screws are difficult to install and often loosen or break after installation, which is one of the major problems reported with dental implants. Other problems include screw loosening problems which lead to increased patient visits for prosthesis maintenance and screw tightening, decreased abutment stability, and abutment screw breakage which sometimes results in the lose of the entire implant site. While the internal and external slot, hex, or spline features provide repeatability of abutment placement and provide a means to apply or resist torque, they do not in of themselves alleviate the associated problems with screw-type connectors. Furthermore, the external hex feature fails to add stability to the connection, since radial clearance must be provided for assembly of the components.

SUMMARY OF THE INVENTION

It is the object of the present invention to provide an abutment system with superior anti-rotation and stability characteristics.

Another object of the invention is to reduce the necessity of removing and reworking the implant connectors due to failure of individual threaded elements.

In summary, the invention uses a combination of an implant anchor, an abutment having a plurality of connection features for connecting to the implant, and a locking pin for locking the abutment into the implant. The invention also provides a retention feature for locking the abutment into the implant consisting of an expandable segmented end having a retention surface positioned to match a cooperatively formed surface in the implant bore. Upon full insertion of the abutment into the implant bore, the segmented end snap-fits into the implant bore, thereby mating the retention surfaces. The abutment also has an axial bore and a locking pin may be threadebly inserted into the abutment bore. Upon full insertion of the locking pin into the abutment bore, the segmented end is prevented from backing-out, thereby locking the abutment within the implant. The implant anchor includes an axial bore on a superior end having inner surface features matching outer surface features of the inferior end of the abutment. The cooperative operation of these features prevents abutment rotation once the abutment is positioned within the implant and also provides indexability for angled abutments. Such anti-rotation features are accomplished with matching splines and flutes machined on the cooperative surfaces between the abutment exterior and the implant bore inner surface.

Other features and objects and advantages of the present invention will become apparent from a reading of the following description as well as a study of the appended drawings.

BRIEF DESCRIPTION OF THE DRAWINGS

A implant abutment system incorporating the features of the invention is depicted in the attached drawings which form a portion of the disclosure and wherein:

FIG. 1 gives a perspective view of the exploded components of the abutment system;

FIG. 2 is sectional view of the assembled components;

FIG. 5A is a sectional view of the abutment system showing the locking pin partially inserted within the abutment and prior to expansion of the segments to engage the inner surface of the implant bore; and FIG. 5B is a sectional view of the abutment system after full insertion of the locking pin and expansion of the segments into locking engagement with the implant bore.

DESCRIPTION OF THE PREFERRED EMBODIMENTS

Figure 3:
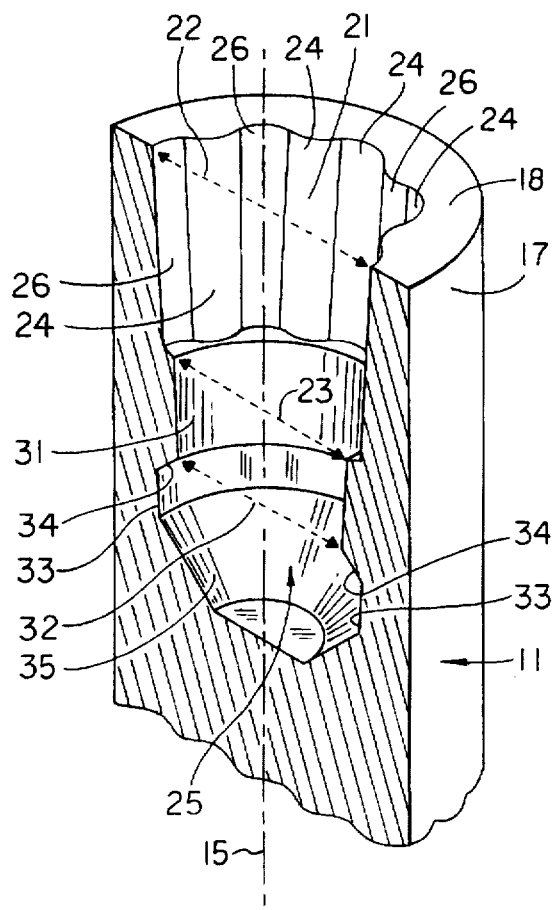
FIG. 3 is an enlarged sectional view of the inner surface of the implant bore showing the complementary inner surface features and inner surface splines.

Referring to the drawings for a better understanding of the function and structure of the invention, it can be seen in FIG. 1 that the abutment system 10 is comprised of three main components; an implant anchor 11, an abutment 42, and a locking pin 90. The combination of these elements is particularly adapted to the field of dental implant prosthetics, however it should be understood that the scope of the invention includes other orthopedic implants. Implant 11 is generally osseointegrated into a targeted human bone as, for example, a human jaw bone. The structure of the inferior end of the implant anchor 11 may be a root-form implant or a blade-form implant. The implant may be also manufactured in any of the following forms to promote bone growth and regeneration: threaded screw-type, cylindrical, stepped surface, hollow cylindrical baskets, or blades. The insertion end of the implant 14 may be configured to be self tapping or tapered to mate with a pre-tapped hole in the jaw bone.

Internally, the implant 14 is conformed for mating engagement with abutment 42. The attachment end 13 of implant 14 includes a constant diameter annulus 17 circumscribing an axial bore. A bearing surface 18, perpendicular to the axis 15 of the implant is formed by the constant diameter annulus 17, and circumscribes a internally recessed frusta-conic section 21 which tapers from a maximum diameter 22 at the bearing surface 18 to a minimum diameter 23, as is more easily seen in FIG. 3. The internally recessed conic section 21 is machined or otherwise formed such that a plurality of longitudinally oriented splines 24 and flutes 26 are formed in the cone surface. The splines 24 and flutes 26 are graduated such that the surface of the conic section 21 has no discontinuities which would serve to increase the stress in any particular area. The conic section 21 is one of several inner surface features of the primary bore 25 which is oriented longitudinally along the axis 15. As will be seen, these surface features in cooperation with correspondingly formed surface features on the abutment provide a means for dispersing the torsional stresses experienced by the implant assembly in application, and provide a means for fixing the abutment into the implant bore. A smooth conic portion 31 begins at the minimum spline diameter 23 and tapers down to the minimum cone diameter 32. An annular groove 33 is machined below the smooth conic portion 31 to form a retention surface 34. The bore 25 terminates subjacent groove 33 with a frusta-conical recess 35 for receiving the lower tip 85 of locking pin 90 once fully inserted.

Figure 4:
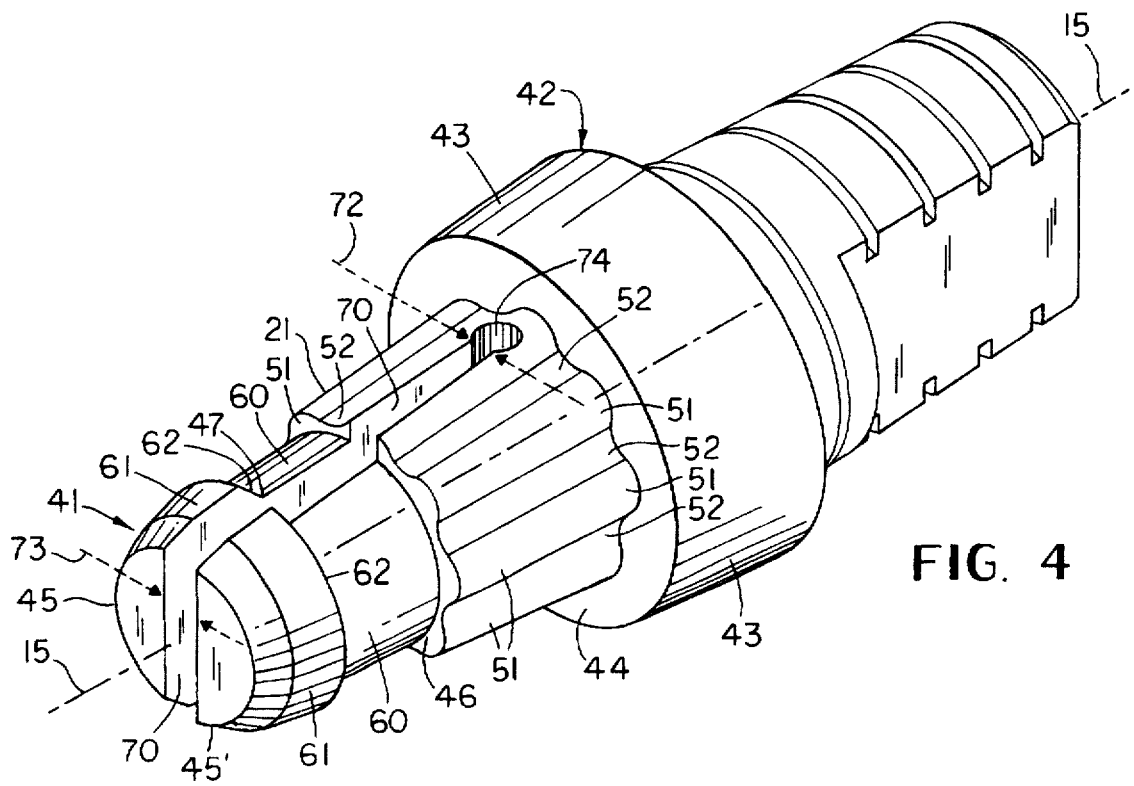
FIG. 4 is a perspective view of the abutment.

As shown in FIGS. 1, 2 and 4, the superior end of the abutment has a plurality of circumferentially oriented grooves and a beveled surface for use as a leverage bearing surface and for prosthetic alignment. The abutment 42 serves to connect the prosthesis to the implant 11 and the grooves facilitate cementation of the prosthesis to the implant as is well known in the art. The abutment also has a lower frusta-conical outer surface 43 terminating in a lower annular surface 44 which is formed for cooperative support on bearing surface 18.

A mating protrusion 41 is circumscribed by the annular surface 44 and tapers toward axis 15 from the surface 44 to a minor diameter 46. The protrusion 41 includes several surface features conforming to the interior surface features of implant bore 25. The protrusion 41 is machined such that the tapered surface has formed thereon a plurality of alternating splines 51 and flutes 52, which register with the splines 24 and flutes 26 of the recessed conic section 21. A smooth frusta-conical surface 60 begins at the minor diameter 46 of the splines and tapers down to a reduced diameter 47. An annular protruding lip 61 is machined below the smooth surface 60 and has a retention surface 62. The lip 61 is designed to register with groove 33 such that the abutment retention surface 62 registers against implant retention surface 34. A downwardly opening vertical slot 70 is milled or otherwise formed through the abutment external protrusion 41 such that two symmetrical segments 45, 45' are formed. The vertical slot 70 has a maximum thickness at 72 and tapers down to a minimum thickness at 73, and slot 70 is terminated at the upper end by circular stop 74. An axial bore 81 is formed through the abutment 42 as shown and has a maximum diameter 82 at a superior end thereof. The midsection of bore 81 is threaded at 84 for engagement with locking pin 90, and a curved retention surface 87 formed below the threaded receptacle. The bore 81 also has a reduced transition diameter section 83 extending to the inferior end.

Referring again to FIGS. 1 and 2, it may be seen that locking pin 90 engages the abutment 42 for the purpose of locking the abutment protrusion 41 into the implant 11 and preventing radial movement of segments 45, 45'. The locking pin 90 is generally cylindrical shaped and has a threaded mid-section 91 which threadedly engages the abutment threads 84. The superior portion of the locking pin 90 includes a constant diameter section 93 connected to the threaded midsection 91 via a transition section 101. The lower or inferior portion of the pin 90 has a reduced diameter section 94, which terminates at a lower conical tip 85. A curved retention surface 92 is machined below the threaded receptacles 91 and serves to form a cooperative surface with the bearing surface 87 of the abutment bore. An axial bore 95 is formed from the top portion of the superior end of the pin and terminates within the threaded section 91 at 99. The bore 95 includes a hexagonally shaped inner surface section 98 starting at 97, and the uppermost section of the bore 95 has a smooth inner surface from a position at 97 to 96 as shown.

As may be seen from the forgoing, the mating surfaces on the exterior of the abutment protrusion 41 and the implant bore 25 are positioned such that the abutment can be seated with precision relative to the implant 11, thereby facilitating alignment of a prosthesis installed on the abutment. Further, the interaction of the cooperative splines and flutes resists torsional loads and prevents angular movement of the abutment relative to the implant without inducing stress raising discontinuities in the interfaces. Thus, torsional loading is not concentrated as may occur with rectangular keys or hex connections. It will also be appreciated that the surface features of the bore 25 provide a means for applying torque to the implant with an insertion tool having a cooperative surface to facilitate seating of the implant within the jaw bone initially.

As shown in FIGS. 5A and 5B, the segmented portions 45, 45' of protrusion 41 deform radially toward axis 15 upon insertion of 41 into implant bore 25 allowing abutment lip 61 to snap into the implant groove 33. When the abutment 42 and implant 11 are properly mated, a cooperative interface resistant to axial and angular movement is formed by the abutment retention surface 62 and the implant retention surface 34, and the mated splines and flutes. When the locking pin 90 is fully inserted into the abutment 42, the segmented portions 45, 45' of the abutment protrusion 41 is prevented from deforming, thereby locking the abutment in place. Locking together of the cooperative features prevents any possibility of axial, lateral, or rotational movement of the abutment relative to the implant, and resists torsional loading and the associated problems discussed in the background.

While I have shown my invention in one form, it will be obvious to those skilled in the art that it is not so limited but is susceptible of various changes and modifications without departing from the spirit thereof. It should also be understood that although much of the foregoing description was directed to a dental implant, the scope of the invention includes other types of orthopedic implants well known to those skilled in the art.

Having set forth the nature of the present invention, what is claimed is:

1. An implant assembly for securing a prosthesis to a bone, comprising:
   a. an implant adapted for osseointegration into a bone, having an axial bore and a longitudinal axis;
   b. an abutment having a radially resilient inferior end conformingly received within said axial bore, and a central axis; and
   c. means for fixing said abutment within said bore of said implant such that said inferior end is fixed against angular movement and axial displacement within said implant bore upon insertion therein, said fixation means comprising a first surface on an interior surface of said implant bore, a conforming surface feature on an exterior of said inferior end of said abutment cooperatively shaped for engagement with said first feature to prevent relative angular displacement, and wherein said inner surface of said implant bore includes an annular groove and said abutment includes an annular protruding lip engagable with said annular groove to prevent axial relative displacement; said inferior end includes a frusta-conical portion extending downward from said abutment, said annular protruding lip, and a reduced diameter section connecting said frusta-conical section to said lip.

2. An implant assembly as recited in claim 1, wherein said abutment further includes an axial bore extending through said abutment, and wherein said assembly includes a locking pin adapted for conforming insertion into said abutment bore so that said inferior end of said abutment is fixed against radial movement.

3. An implant assembly as recited in claim 1, wherein said abutment includes a plurality of resilient segments.

4. An implant assembly as recited in claim 3, wherein said abutment further includes an axial bore extending through said abutment, and wherein said assembly includes a locking pin adapted for conforming insertion into said abutment bore so that said inferior end of said abutment is fixed against radial movement.

5. An implant assembly as recited in claim 4, wherein said first surface feature comprises a plurality of graduated alternating flutes and splines and said conforming surface feature comprises a plurality of cooperatively formed flutes and splines on said exterior of said inferior end.

6. An implant assembly as recited in claim 5, wherein each said segment comprises a frusta-conical radial section extending downward from said abutment, a radial section of said annular protruding lip, and a reduced diameter radial section connecting said frusta-conical section to said lip, said segments defining a plurality of axial slots.

7. An implant assembly as recited in claim 6, wherein said plurality of alternating flutes and splines are positioned on an exterior surface of said frusta-conical section.

8. An implant assembly as recited in claim 3, wherein and said conforming surface feature on said exterior of said inferior end comprises a plurality of alternating flutes and splines.

9. An implant assembly as recited in claim 8, wherein each said segment comprises a frusta-conical radial section extending downward from said abutment, a radial section of said annular protruding lip, and a reduced diameter radial section connecting said frusta-conical section to said lip, said segments defining a plurality of axial slots.

10. An implant assembly as recited in claim 9, wherein said plurality of alternating flutes and splines are positioned on an exterior surface of said frusta-conical section.

11. An implant assembly as recited in claim 1, wherein said first surface feature comprises a plurality of alternating flutes and splines and said conforming surface feature comprises a plurality of flutes and splines on an exterior surface of said frusta-conical portion.

12. An implant assembly for securing a prosthesis to a bone, comprising:
   a. a generally cylindrically shaped implant having a osteo-promoting inferior end and an axially aligned bore, said bore including a frusta-conical interior surface section and an annular groove below said conical section;
   b. an abutment having a resilient and segmented inferior end received within said segmented inferior implant bore, said end including lip means for effecting conforming engagement of said segmented inferior end within said groove, wherein said segmented inferior end includes means distributed over an exterior surface thereof for preventing angular movement of said abutment within said implant, said abutment further including an axial bore extending therethrough; and
   c. a locking pin having a lower portion received within said abutment bore for bearing against an interior surface of said segments such that said segments are fixed against radial movement.

13. An implant assembly as recited in claim 12, wherein said lip means comprises an annular protruding lip engageable with said annular groove to prevent axial movement of said abutment.

14. An implant assembly as recited in claim 13, wherein said exterior surface means comprises a plurality of axially aligned alternating splines and flutes engagable with a plurality of cooperatively formed splines and flutes on said frusta-conical interior surface section of said implant bore.

15. An implant assembly for securing a prosthesis to a bone, comprising:
   a. an implant having a osteo-promoting inferior end and an axially aligned bore, said bore including a frusta-conical interior surface section and an annular groove below said conical section;
   b. an abutment having a resilient inferior end received within said bore and including lip means for effecting conforming engagement of said resilient inferior end within said groove, wherein said resilient inferior end includes means distributed over an exterior surface thereof for preventing angular movement of said abutment within said implant, said abutment further including an axial bore extending through said abutment; and
   c. locking pin means received within said axial bore of said abutment for preventing radial movement of said resilient inferior end such that said inferior end is locked into said implant.

16. An implant assembly as recited in claim 15, wherein said lip means comprises an annular protruding lip engageable with said annular groove to prevent axial displacement of said abutment.

17. An implant assembly as recited in claim 15, wherein said means distributed over an exterior surface thereof comprises a plurality of axially aligned alternating splines and flutes engagable with a plurality of cooperatively formed splines and flutes on an interior surface of said implant bore.

18. An implant assembly for securing a prosthesis to a bone, comprising:
   a. a generally cylindrically shaped implant having a osteo-promoting inferior end and an axially aligned bore, said bore including a frusta-conical interior surface section and an annular groove below said conical section;
   b. an abutment having a resilient and segmented inferior end received within said implant bore, said segmented inferior end including lip means for effecting conforming engagement of said segmented inferior end within said groove, said abutment further including an axial bore extending therethrough; and
   c. a locking pin having a lower portion received within said abutment bore for bearing against an interior surface of said segments such that said segments are fixed against radial movement.

* * * * *